United States Patent
Lyons et al.

(10) Patent No.: US 7,291,181 B1
(45) Date of Patent: Nov. 6, 2007

(54) STUMP BOOT FOR AN ANKLE DISARTICULATION PATIENT

(76) Inventors: Joseph Lyons, 12621 Tinley Rd., New Port Richey, FL (US) 34654; George Brown, 8811 Dusty La., New Port Richey, FL (US) 34655-1001

( * ) Notice: Subject to any disclaimer, the term of this patent is extended or adjusted under 35 U.S.C. 154(b) by 201 days.

(21) Appl. No.: 11/088,444

(22) Filed: Mar. 24, 2005

(51) Int. Cl.
  *A61F 2/60* (2006.01)
  *A61F 2/80* (2006.01)

(52) U.S. Cl. .......................... 623/33; 623/36

(58) Field of Classification Search ............ 623/32–37; 602/10, 65, 62
See application file for complete search history.

(56) References Cited

U.S. PATENT DOCUMENTS

| | | | |
|---|---|---|---|
| 5,019,064 A | 5/1991 | Eilender | 530/189 |
| 5,154,682 A | 10/1992 | Kellerman | 36/44 |
| 5,224,810 A | 7/1993 | Pitkin | 36/30 |
| 5,317,819 A | 6/1994 | Ellis, III | 36/25 |
| 5,544,429 A | 8/1996 | Ellis, III | 36/25 |
| 5,695,526 A | 12/1997 | Wilson | 623/49 |
| 5,728,165 A * | 3/1998 | Brown, Sr. | 623/33 |
| 5,797,862 A | 8/1998 | Lamont | 602/10 |
| 6,115,945 A | 9/2000 | Ellis, III | 36/102 |
| 6,362,387 B1 | 3/2002 | Carlson et al. | 602/41 |
| 6,470,599 B1 | 10/2002 | Chu | 36/113 |
| 6,514,293 B1 | 2/2003 | Jang et al. | 623/55 |

* cited by examiner

*Primary Examiner*—Bruce Snow
(74) *Attorney, Agent, or Firm*—Law Offices of J.D. Geraigery, P.C.; Janine D. Geraigery

(57) ABSTRACT

A stump boot for use by an ankle disarticulation patient having a stump. The stump boot includes a sole, an inner casing, and an outer casing having a substantially rectangular cutout covered by a flexible member. The inner casing is custom molded to fit the stump and insertable within the outer casing. The sole is integrally attached to the outer casing and includes a foam inner sole, an outer sole having a non-skid grip material, a contoured wedge therebetween having an adjustable rubber build-up and a rounded bottom. A buckle and a strap are both integrally attached to the outer casing opposite one another. The strap has a securing fastener and a securing means and wraps over the flexible member and through the buckle for securing the stump within the stump boot.

3 Claims, 3 Drawing Sheets

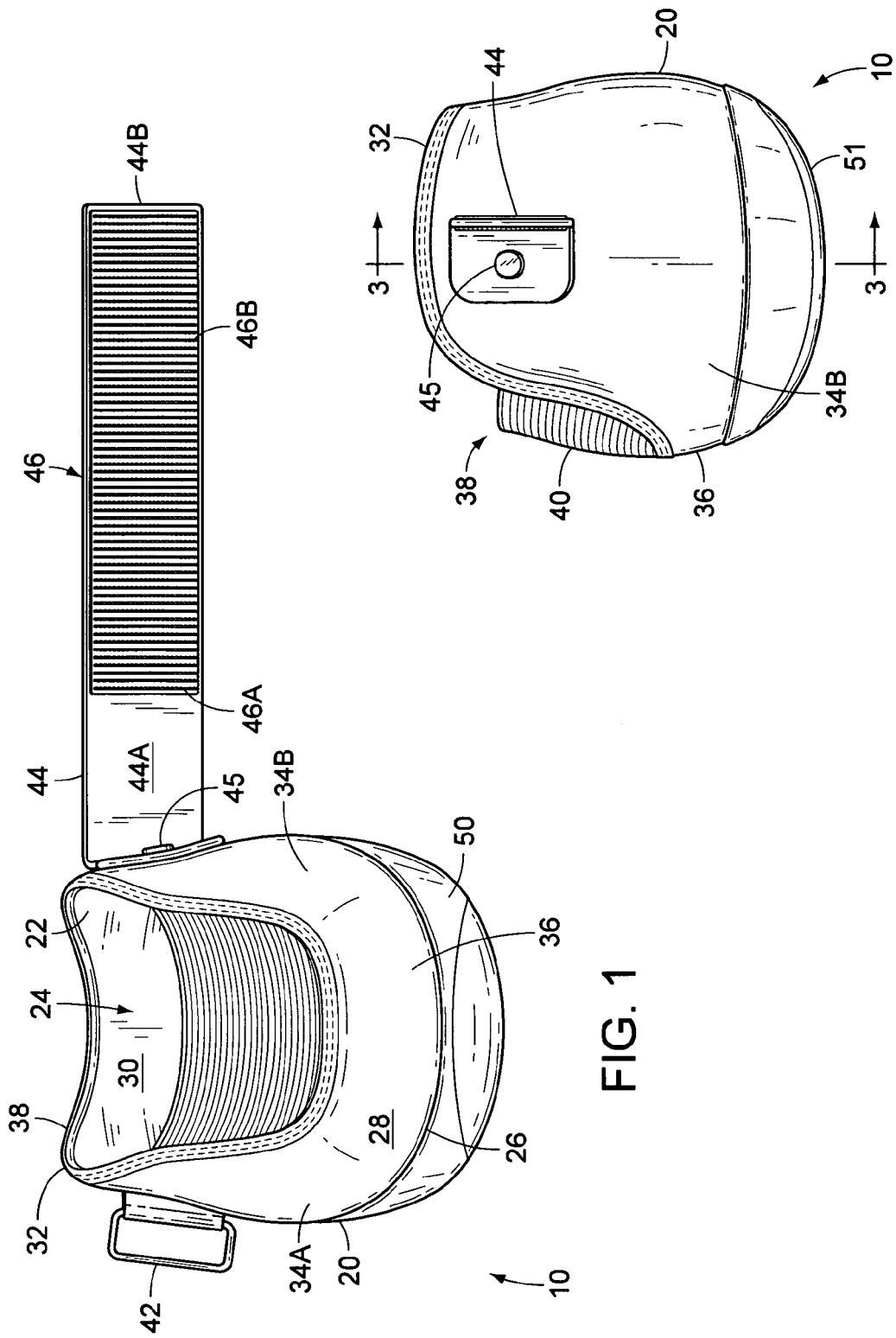

STUMP BOOT FOR AN ANKLE DISARTICULATION PATIENT

BACKGROUND OF THE INVENTION

The invention relates to a prosthetic device, and more particularly to a stump boot for an ankle disarticulation patient, or Syme's amputation, for eliminating the build up of scare tissue and callous formation in said stump boot wearer.

The Syme technique of amputation has existed since 1842. Named after James Syme, and referred to as a disarticulation at the ankle, the surgical amputation at the ankle involves removal of the malleoli and forward rotation of the heel pad over the end of the residual tibia. The disarticulation is performed through the ankle joint with preservation on the heel pad to permit weight-bearing at the end of the stump. The ankle joint consists of three bones including the tibia which forms the inside, or medial, portion of the ankle, the fibula which forms the lateral, or outside portion of the ankle, and the talus underneath. The ankle joint is responsible for up and down motion of the foot. The Syme's amputation cuts through the ankle joint while maintaining the tough, durable skin of the heel pad. The heel pad must be intact and accurately applied as it is crucial for weight-bearing and protecting the cut surface of the tibia and fibula. The Syme's amputee continues to bear weight in the residual foot while experiencing sensation and proprioception, the ability to feel position and surface.

The Syme's amputation is mainly used for foot deformities, which cannot be corrected to a plantigrade position, fibular hemimelia and severe foot injury, as long as the heel pad remains intact, vascular insufficiency, with or without diabetes, and for infections of the forefoot. The process for a Syme's amputation must be exact in order to provide the amputee with the greatest benefits.

The significant outcome of Syme's technique for those wearing a prostheses, is that the patient has a foundation to walk on instead of cutting off the entire leg. However, surgeons are reluctant to perform the operation. The cause of the hesitancy is centered around the manufacture and use of the prosthesis fitted afterward. In fact, the most common problem with lower limb amputations is prosthetic fittings. The Syme's amputee is left with an end bearing stump that requires the use of a prosthesis when walking to prevent the heel pad from losing its essential position. The prosthesis used must accommodate the flair of the distal tibial metaphysic that is covered with heavy plantar skin and thus is rather large and bulky. For this reason the amputation is usually not recommended for women. Additionally, painful neuroma and impairment of the blood supply can result when dressings are applied too tightly to a Syme's amputee. Sometimes, swelling occurs beneath adhesive strappings that are not removed soon enough.

In the Syme's amputation the resulting stump tissue that is preserved is constructed by nature to bear weight and to deliver sensory feedback from walking. Since the stump has more surface area and the leg has a longer lever arm, the amputee has considerable enhanced control of their leg movements.

Typical prosthesis devices are self-suspending and therefore there is little or no positioning of the prosthesis during the transition from swing phase to stance phase. However, there are many obstacles involved in properly fitting the prosthetic device. Not only must the prosthesis fit comfortably, but heat and perspiration must also be considered. The intricate process of making the device, the difficulty of fitting the device, and the frequent structural failures and poor cosmesis must all be taken into consideration. In addition, the stump is often tender on weight-bearing and results in callous formation.

The stump boot of the present invention eliminates complications associated with prosthetic devices and allows patients, both male and female, to receive mobility and independence not otherwise afforded.

Prosthetic devices are generally known in the art. U.S. Pat. Nos. 5,317,819 and 5,544,429 to Ellis, III both disclose an athletic shoe having a sole that conforms to the natural shape of the foot, particularly the sides, and that has a constant thickness in frontal plane cross sections. The thickness of the shoe sole side contour equals and therefore varies exactly as the thickness of the load-bearing sole portion varies due to heel lift, for example. U.S. Pat. No. 6,115,945 also to Ellis III discloses an athletic shoe having a sole that conforms to the natural shape of the foot, including a bottom and sides when the foot sole deforms naturally by flattening under load while walking or running in order to provide a stable support base for the foot and ankle. Deformation sipes such as slits or channels are introduced in the shoe sole along its axis, and other axes, to provide it with flexibility roughly equivalent to that of the foot. The result is a shoe sole that accurately parallels the frontal plane deformation of the foot sole, which create a stable base that is wide and flat even when tilted sideways in extreme pronation or supination motion.

U.S. Pat. No. 5,797,862 to Lamount discloses a protective boot for patients with arterial disease having an insole formed with a heat activated material to form a permanent impression of the bottom of a patient's foot.

U.S. Pat. No. 6,470,599 to Chu discloses a climbing shoe having an inner sole, an outer sole and a molded middle sole between the inner and outer sole. The middle sole is concave in shape. The outer sole conforms to the concave shape of the middle sole. The concave shape allows the outer sole to hook on a rocky ledge. The molded middle sole provides a structure that causes the concave outer sole to substantially maintain the concave shape when pressure is applied to the outer sole.

U.S. Pat. No. 5,224,810 to Pitkin discloses an athletic shoe providing a safe orientation of the foot during an immediate stop in the medial lateral direction and to preclude hyperinversion of the foot in the subtalar joint.

U.S. Pat. No. 5,154,682 to Kellerman discloses a low friction shoe insert of ultrahigh molecular weight polyethylene or the like having a coefficient of friction of 0.3 or less with an array of detachable discrete cushion elements on the shoe contacting lower surface to both frictionally anchor the insert to the shoe and permit the shape to be customized to the wearer's foot and selectively relieve pressure on painful and sensitive areas.

U.S. Pat. No. 5,019,064 to Eilender discloses a multilayer low friction pad for reducing shear and friction forces on a person's body, and for preventing and treating sores on a person's body caused by shear forces, friction, pressure, chafing and moisture.

U.S. Pat. No. 6,362,387 to Carlson et al., discloses a patch of low friction materials, such as a film of polytetrafluoroethylene sized to provide an area of low friction support for a portion of a human body relative to an object such as a shoe or prosthetic socket. The patch can be lined with foam, or preferably, a stretch fabric so that it will fit around irregular contours of the shoe, socket, or the skin itself. The patches reduce shear trauma in critical load areas. After identifying regions of high loads, the method comprises applying the patches as needed to avoid sores, calluses, blisters and abrasions.

U.S. Pat. No. 6,514,293 to Jang et al. discloses a prosthetic foot that is to be connected to a pylon that is utilized for the substitution of the shinbone of an amputee.

U.S. Pat. No. 5,695,526 to Wilson discloses a one-piece mechanically differentiated prosthetic foot and associated ankle joint with Syme modification.

U.S. Pat. No. 6,811,571 to Phillips discloses a cushioned ankle prosthetic foot and a cosmesis having a slot between the big toe and adjacent toe to allow the amputee to wear thong sandals and the like. U.S. Pat. Nos. 5,993,488 and 5,800,569 to Phillips disclose prosthesis with resilient ankle block. U.S. Pat. No. 5,728,177 also to Phillips discloses a prosthesis with foam block ankle. U.S. Pat. No. 5,549,714 also to Phillips discloses a Symes foot prosthesis. U.S. Pat. No. 5,376,141 also to Phillips discloses a low-profile Syme's foot prosthesis.

U.S. Pat. No. 6,406,499 to Kania discloses an annular sleeve configured to receive a limb and having a gel composition containing a block copolymer and mineral oil. U.S. Pat. No. 5,653,768 also to Kania discloses a dual cantilevered leaf spring structure for providing a prosthesis for an amputee.

U.S. Pat. No. 4,225,982 to Cochrane et al. discloses a molded Syme foot with attached stump socket having a flexible pre-cast foot comprising a hollow flexible slipper member which has a rounded heel contour and keel cavity.

U.S. Pat. No. 5,545,230 to Kinsinger et al. discloses a prosthesis mounting adapter and method. U.S. Pat. No. 6,261,324 to Merlette discloses a foot prosthesis. U.S. Pat. No. 5,030,239 to Copes discloses a biomechanical ankle. U.S. Pat. No. 4,923,476 to Cooper et al. discloses an alignment device and method of artificial limb manufacture. U.S. Pat. No. 6,562,075 to Townsend et al. discloses a prosthetic foot with tunable performance.

While these units may be suitable for the particular purpose employed, or for general use, they would not be as suitable for the purposes of the present invention as disclosed hereafter.

SUMMARY OF THE INVENTION

It is an object of the invention to produce a means for increasing mobility and independence for a Syme's amputation patient. Accordingly, the invention is a lightweight stump boot for wear by a Syme's amputee patient having disarticulation at the ankle.

It is another object of the invention to provide a means for increasing an amputee's control over their movements while eliminating problems associated with self-suspending prosthesis especially during the transition from swing phase to stance phase. Accordingly, the stump boot of the invention includes a durable and compact outer casing covering an inner casing and a rounded sole which affords the amputee increased control over their movements while eliminating the self-suspending and positioning problems occurring during the transition from swing phase to stance phase.

It is another object of the invention to provide a pain free means of walking while eliminating blood poisoning for those with diabetes, and other blood circulation complications cause by the currently available prosthetic devices. Accordingly, the inner casing is custom manufactured from reinforced plastic and the like, from a negative plaster mold made and fitted to each amputee for fitting securely around the stump but still allowing blood to flow naturally and thereby eliminating blood poisoning and poor blood circulation complications while walking pain free.

It is another object of the invention to prevent the build-up of scar tissue and calluses caused by prosthetic devices. Accordingly, the invention includes a sole having a foam inner sole and a rounded bottom for allowing the weight-bearing stump to equally and adequately accommodate weight as the stump rolls forward pressing against the foam inner sole during walking thereby eliminating the build-up of scar tissue and calluses caused by prosthetic devices that are not properly designed and fitted.

It is another object of the invention to eliminate concerns from resulting poor cosmesis while accommodating the heavy plantar skin of the stump which can be rather large and bulky. Accordingly, the inner casing is custom manufactured to properly fit each stump thereby accommodating the heavy plantar skin. In addition, because the stump boot is compact and lightweight the stump can easily fit therein and mask poor cosmesis.

It is another object of the invention to provide a stump boot capable of accommodating heat and perspiration. Accordingly, the stump boot is able to circulate air therethrough because the outer casing is made of a breathable material, preferably leather and the inner casing is not fitted too tightly, thereby allowing air to circulate for eliminating heat and perspiration problems.

It is another object of the invention to provide a means for easily inserting the stump into the stump boot and securely and comfortably holding the stump within the outer casing. Accordingly, the outer casing of the invention includes a substantially rectangular cutout covered by a flexible member which stretches to accommodate insertion of the stump within the stump boot while securely embracing the stump therein during walking.

It is another object of the invention to provide a means for securely fastening the stump boot to the stump of the amputee. Accordingly, the outer casing of the invention includes a buckle and a strap having a securing means, preferably a hook-and-loop fastener, whereby the strap sweeps around the outer casing through the buckle and secures to itself by a securing means.

This invention is a stump boot for use by an ankle disarticulation patient having a stump. The stump boot includes a sole, an inner casing, and an outer casing having a substantially rectangular cutout covered by a flexible member. The inner casing is custom molded to fit the stump and insertable within the outer casing. The sole is integrally attached to the outer casing and includes a foam inner sole, an outer sole having a non-skid grip material, a contoured wedge therebetween having an adjustable rubber build-up and a rounded bottom. A buckle and a strap are both integrally attached to the outer casing opposite one another. The strap has a securing fastener and a securing means and wraps over the flexible member and through the buckle for securing the stump within the stump boot.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

FIG. 1 is a diagrammatic perspective view of a stump boot for a patient with disarticulation at the ankle having an outer casing, an inner casing, a strap, a buckle, and a rounded sole.

FIG. 2 is a side elevational view of the stump boot of the present invention wherein the strap is coupled to the outer casing by a rivet for securing the stump boot around the stump of the wearer.

DETAILED DESCRIPTION OF THE PREFERRED EMBODIMENTS

Figure 4:
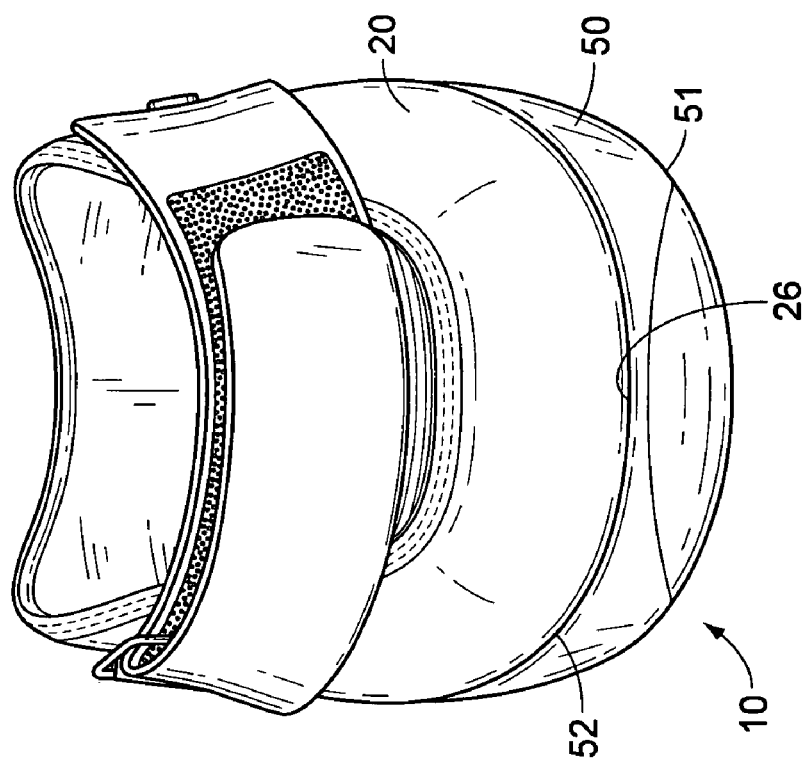
FIG. 4 is a front plan view of the preferred embodiment of the stump boot of the present invention wherein the strap has a securing fastener being a hook-and-loop fastener.

FIG. 1 illustrates a stump boot 10 of the present invention for a patient with disarticulation at the ankle, or more commonly referred to as a Syme's amputation. The stump boot 10 is lightweight yet sturdy and durable and provides amputees wearing said invention with increased mobility and independence without the pain and complications associate with currently available prosthetic devices. The stump boot 10 easily fits over the stump of the amputee and securely fastens therearound for allowing amputees to walk about easily.

The stump boot 10 includes an outer casing 20, an inner casing, and a sole 50. The outer casing 20 is substantially circular and defines an interior hollow cavity 22 between a top opening 24 and a contoured bottom portion 26. Preferably, the outer casing 20 is made of a leather material for maximum durability and protection. The outer casing 20 includes an exterior surface 28, an interior surface 30 and a top edge 32 defining the top opening 24. Because the outer casing 20 is compact lightweight and durable, the stump boot 10 of the invention affords the amputee increased control over their movements.

The outer casing 20 has two side portions 34, including an inner side portion 34A and an outer side portion 34B continuously spaced between a front portion 36 and a rear portion 38 altogether defining the continuous exterior surface 28. The top edge 32 of the outer casing 20 contours upwardly about the two side portions 34 for added support about an ankle. The top edge 32 extends downwardly across the rear portion 38 of the outer casing 20 for increasing comfort to the amputee therealong. Referring to FIGS. 1 and 2, the top edge 32 extends downwardly along the front portion 36 defining a substantially rectangular cutout 38. The cutout 38 is substantially covered by a flexible member 40, preferably elastic, extending thereacross. The flexible member 40 extends outwardly across the front portion 36 and is surrounded on three sides by the top edge 32. The flexible member 40 stretches to accommodate the stump of the wearer inserted within the outer casing 20 while still providing ample support by embracing the stump safely within the outer casing 20 during walking.

Referring to FIG. 1, a buckle 42 is integrally attached to the outer casing 20 on the inner side portion 34A. Referring to FIGS. 1 and 2, a strap 44 is attached parallel from the buckle 42 along the outer side portion 34B of the outer casing 20. The strap 44 is coupled to the outer side portion 34B by a rivet 45. Preferably, the strap 44 is able to rotate about the rivet 45 for maximum support and comfort while in use.

The strap 44 includes a first side 44A and a free end 44B. The strap includes a securing fastener 46, preferably a hook-and-loop fastener having a hook strip 46A and a loop strip 46B, wherein the hook strip 46A is a securing means. Here, the first side 44A of the strap 44 near the free end 44B includes the integrally attached loop strip 46B, alternating between the integrally attached hook strip 46A of the hook-and-loop fastener. The amputee can put the stump boot 10 on by inserting there stump within the outer casing 20 and then as shown in FIG. 4 wrap the free end 44B of the strap 44 across the front portion 36 and through the buckle 42 and fasten the hook strip 46A to the loop strip 46B of said strap 44.

Figure 3:
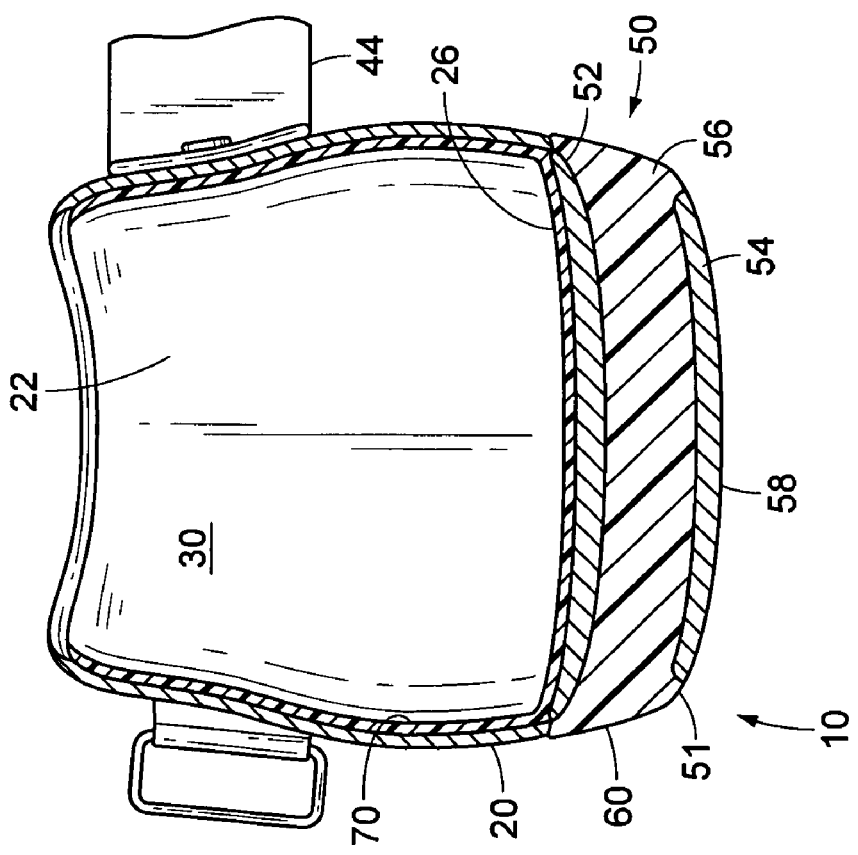
FIG. 3 is a cross-sectional view of the stump boot of the present invention wherein the inner casing is custom manufactured from reinforced plastic and the like, for fitting securely around the stump of the wearer and the rounded sole includes an inner sole, an outer sole and a contoured wedge extending therebetween.

FIG. 3 illustrates a cross-sectional view of the stump boot 10 of the present invention wherein the inner casing 70 is shown. Preferably, the inner casing 70 is custom manufactured from reinforced plastic and the like, from a negative plaster mold for fitting securely around the stump of the amputee. The inner casing 70 would be custom molded and fitted to each and every amputee. By being custom manufactured to fit properly, the inner casing 70 accommodates the heavy plantar skin of the stump which can be rather large and bulky. In addition, because the stump boot 10 is compact and lightweight the stump can easily fit therein and mask poor cosmesis. Because the stump boot 10 absolves poor cosmesis complications and accommodates heavy plantar skin, more women can receive the Syme's amputation and increase their mobility and independence, something not otherwise afforded them.

Additionally, the stump boot 10 and inner casing 70 fit securely enough while still allowing blood to flow naturally through the stump thereby eliminating complications like blood infections and pain caused therefrom. Heat and perspiration do not pose any complications with the stump boot 10 because the inner and outer casings 70 and 20 are breathable and relatively cool. Preferably, the outer casing 20 is made of leather which allows air to freely enter and exit and thereby allows the wearer to perspire without any complication. Furthermore, because only a small area of the stump is placed within the stump boot 10 the leg of the wearer is exposed as normal.

Once fitted to the stump, the inner casing 70 is inserted into the interior hollow cavity 22 of the outer casing 20 and held securely in place against the interior surface 30 of the outer casing 20 by the flexible member and strap 44. Preferably, the inner casing 70 is approximately five and one-half inches in height, four inches in width, five inches in circumference length and four inches in depth.

The sole 50 of the stump boot 10 is integrally attached to the contoured bottom portion 26 of the outer casing 20 and has a rounded bottom 51, shown in FIGS. 2 and 4, for allowing wearers to walk pain free. The Syme's amputee has a locked ankle after the surgery, which makes walking difficult. The rounded bottom 51 compensates for the amputee's lack of an ankle while accommodating inconsistencies in ground surfaces. Furthermore, the rounded bottom 51 allows the weight-bearing stump to equally and adequately accommodate weight as the amputee's stump rolls forward and backward against the rounded bottom 51 within the outer casing 20 during walking. The rounded bottom 50 of the stump boot 10 compensates for the absence of the ankle joint and allows the amputee to roll therealong the rounded bottom 51 with each and every step. The rounded bottom 51 is therefore useful in preventing the build-up of scar tissue and calluses caused by common prosthetic devices that do not adequately accommodate weight-bearing and walking.

The sole 50 of the stump boot 10 includes an inner sole 52, an outer sole 54 and a contoured wedge 56 extending therebetween. The inner sole 52 is attached against the contoured bottom portion 26 of the outer casing 20. Preferably, the inner sole 52 is made of foam and provides a cushioned support for the stump when weight is pressed thereagainst. The foam inner sole 52 and rounded bottom 51 allow the weight-bearing stump to equally and adequately accommodate weight as the stump rolls forward pressing against the foam inner sole 52 during walking thereby eliminating the build-up of scar tissue and calluses caused by prosthetic devices that are not properly designed and fitted. The resiliency of the rounded bottom 51 and inner sole 52 are controlled by the type of foam used in order that the compressibility of the stump may be varied during construction.

The outer sole 54 comes in contact with ground surfaces and includes non-skid grip material 58 integrally attached thereto for increasing stability to the wearer while preventing slipping and falling. Preferably, the sole 50 is nine inches in circumference.

The contoured wedge 56 is preferably a rubber build-up that extends between the inner and outer soles 52 and 54 and includes an adjustable height 60 which changes to accommodate heights of different ankle joints after a Syme's amputation.

Figure 5:
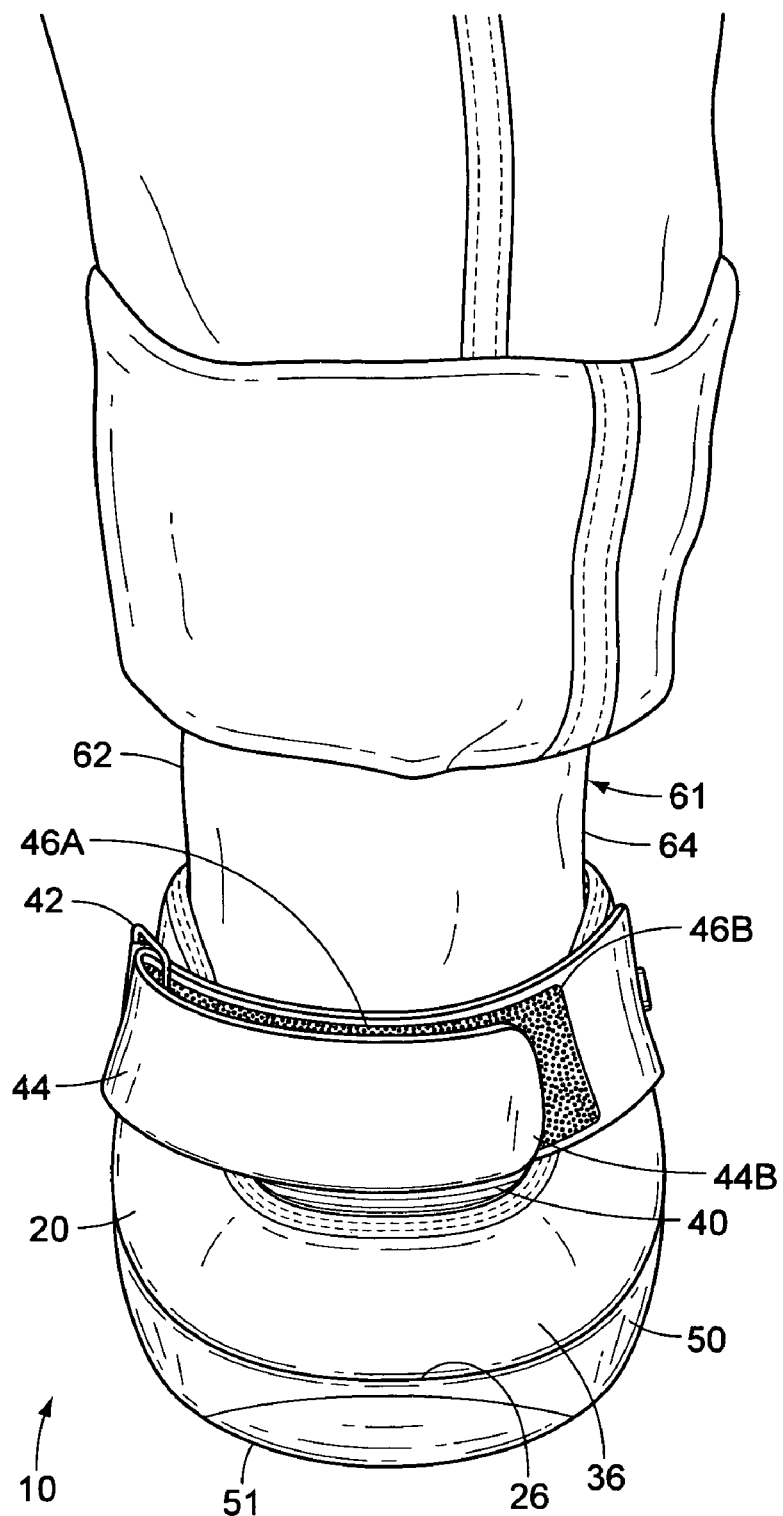
FIG. 5 is a diagrammatic perspective view of the stump boot of the present invention in use by a Syme's amputee patient having disarticulation at the ankle.

FIG. 5 illustrates the stump boot 10 in use. The stump boot 10 is shown here being used on the wearer's left foot, but the identical stump boot 10 could also be used on the right foot, as the boot 10 is essentially symmetrical about a central vertical plane.

The Syme's amputee has a leg 61 having an inner an outer portion 62 and 64 and a stump. In use, the amputee places their stump into an inner casing molded specifically to fit their stump. Next, with the flexible member 40 of the outer casing 20 facing forward, the inner casing and stump are inserted into interior hollow cavity between a top opening by stretching the flexible member 40. The contoured bottom portion 26 of the outer casing 20 is positioned such that the top edge 32 of the outer casing 20 contours upwardly about the inner and outer portions 62 and 64 of the leg 61. The outer casing 20 is designed to hug and support the inner casing 70 therein. Then, the amputee wraps the free end 44B of the strap 44 across the front portion 36 and flexible member 40, through the buckle 42, and tightly fastens the hook side 46A to the loop side 46B of the strap 44. The amputee is then able to walk freely while allowing the curved bottom 51 of the sole 50 to move naturally along a ground surface. The amputee walks by bearing weight from the stump down onto the foam inner sole and causing the rounded bottom 51 of the sole 50 to roll forward against the ground surface and compensate for lack of normal ankle movement resulting from Syme's amputation.

In addition, while the inner and outer casings are light and cosmetic and therefore easy to wear, they will not easily buckle as ordinary prosthetic devices do because they are made preferably from leather and a prefabricated plastic molding.

In conclusion, herein is presented a stump boot for a patient with disarticulation at the ankle. The invention is illustrated by example in the drawing figures, and throughout the written description. It should be understood that numerous variations are possible, while adhering to the inventive concept. Such variations are contemplated as being a part of the present invention.

What is claimed is:

1. A stump boot for use by an ankle disarticulation patient having a stump, comprising:

a substantially circular outer casing defining an interior hollow cavity between a top opening and a contoured bottom portion, said casing having an exterior surface, an interior surface, and a top edge defining the top opening, said exterior surface has two side portions, including an inner and outer side portion, and having a front and rear portion together defining a continuous exterior surface, said top edge contouring upwardly about the two side portions and extending downwardly across the rear portion, said top edge extending downwardly along the front portion and defining a substantially rectangular cutout being covered by a flexible member extending thereacross, said flexible member extending outwardly across the front portion and being partially surrounded by said top edge;

a buckle integrally attached to the inner side portion of the exterior surface of the outer casing;

a strap having a first side, a free end, and a securing fastener including a hook-and-loop fastener having a hook strip and a loop strip, wherein the hook strip is a securing means, said first side of the strap near the free end includes the loop strip integrally attached thereto alternating between the hook strip integrally attached thereto, said strap attaching by a rivet to the outer side portion of the exterior surface of the outer casing opposite the buckle;

an inner casing custom manufactured from reinforced plastic from a negative plastic mold to fit the stump and insertable against the interior surface of the outer casing and held in place by the strap and flexible member; and a sole having a rounded bottom and being integrally attached to the contoured bottom portion of the outer casing, said sole including a foam inner sole, an outer sole, and a contoured wedge extending therebetween, said foam inner sole integrally attached against the contoured bottom portion of the outer casing, said outer sole having contact with a ground surface and including a non-skid grip material, said contoured wedge being an adjustable rubber build-up and extending between the inner and outer soles.

2. The stump boot of claim 1, wherein the flexible member is elastic.

3. A method of walking by an ankle disarticulation patient having a stump, and a leg having an inner and outer portion, wearing a stump boot having an inner casing, an outer casing having an interior hollow cavity having a flexible member, a strap having a free end having a securing fastener having a securing means, having a sole having a rounded bottom, a foam inner sole, and an outer sole, the steps comprising:

a) inserting the stump into the stump boot by putting the stump into the inner casing and placing the inner casing into the interior hollow cavity of the outer casing by stretching the flexible member;

b) securing the stump within the stump boot by wrapping the free end of the strap across the flexible member and through the buckle and attaching the securing means to the securing fastener; and c) walking by bearing weight from the stump down onto the foam inner sole and causing the rounded bottom of the sole to roll forward against a ground surface and compensate for lack of normal ankle movement.

\* \* \* \* \*